US012702814B1

(12) United States Patent
Nijland et al.

(10) Patent No.: US 12,702,814 B1
(45) Date of Patent: Aug. 11, 2026

(54) PRESSURE CONTROLLED VALVE

(71) Applicant: Minivalve International B.V., Oldenzaal (NL)

(72) Inventors: Peter Lodewijk Joannes Nijland, De Lutte (NL); Niels Scholten, Denekamp (NL); Dimitrios Christianus Siepman, Denekamp (NL); Jeffrey A. Carlisle, Portsmouth, NH (US); Miranda N. Bakos, Boston, MA (US)

(73) Assignee: Minivalve International B.V., Oldenzaal (NL)

( * ) Notice: Subject to any disclaimer, the term of this patent is extended or adjusted under 35 U.S.C. 154(b) by 0 days.

(21) Appl. No.: 19/095,851

(22) Filed: Mar. 31, 2025

(51) Int. Cl.
*A61M 39/22* (2006.01)
*F16K 7/17* (2006.01)

(52) U.S. Cl.
CPC ............. *A61M 39/227* (2013.01); *F16K 7/17* (2013.01)

(58) Field of Classification Search
CPC ............................... A61M 39/227; F16K 7/17
See application file for complete search history.

(56) References Cited

U.S. PATENT DOCUMENTS 3,746,036 A * 7/1973 Du Bois ................. F16K 24/00 137/496
3,773,073 A * 11/1973 Brown ...................... F16K 7/17 137/496
4,581,624 A * 4/1986 O'Connor ................. F15C 5/00 216/2
4,615,693 A 10/1986 Paradis et al.
4,998,562 A 3/1991 Foltz
5,076,322 A * 12/1991 Choksi ................. G05D 16/065 137/505.38
5,762,314 A * 6/1998 Williams .................. F16K 7/17 251/367
6,145,695 A * 11/2000 Garrigues ................ B62J 11/16 222/61
6,290,682 B1 * 9/2001 Myers ....................... F16K 7/17 604/247

(Continued)

OTHER PUBLICATIONS

Mosadegh, B., et al., "Integrated Elastomeric Components for Autonomous Regulation of Sequential and Oscillatory Flow Switching in Microfluidic Devices." Nat Phys. Jun. 1, 2010;6(6):433-437.

*Primary Examiner* — Daphne M Barry
(74) *Attorney, Agent, or Firm* — Nutter McClennen & Fish LLP

(57) ABSTRACT

A medical valve has a first port, a second port, a control port, and a fluid channel the ports. The valve also has a normally non-flat diaphragm within a housing configured to isolate the control port from the fluid channel, first port, and the second port. The diaphragm controls fluid flow through the fluid channel in response to four forces: 1. a first force generated on the diaphragm from a differential fluid pressure between the first port and the control port times the exposed surface area of the diaphragm, 2. a second force generated on the diaphragm from a differential fluid pressure between the second port and the control port times the exposed surface area of the diaphragm, 3. a third force generated by elastic deformation of the diaphragm, and 4. a fourth force generated by a pressure drop due to fluid flow in the fluid channel due to the Venturi effect.

22 Claims, 16 Drawing Sheets

(56) References Cited

U.S. PATENT DOCUMENTS

| | | | | |
|---|---|---|---|---|
| 7,537,133 | B2 * | 5/2009 | Naesje | B65D 47/243 220/717 |
| 8,066,648 | B1 | 11/2011 | Mark | |
| 8,920,645 | B2 | 12/2014 | Moran et al. | |
| 9,239,119 | B2 * | 1/2016 | Morris | F16K 7/17 |
| 9,574,674 | B2 * | 2/2017 | Maeda | F16K 15/144 |
| 9,803,755 | B2 * | 10/2017 | Weingarten | F16K 7/17 |
| 9,976,660 | B2 | 5/2018 | Stanton et al. | |
| 10,024,442 | B2 * | 7/2018 | Maenz | A61M 1/14 |
| 10,100,939 | B2 | 10/2018 | Ichiki et al. | |
| 10,344,876 | B2 | 7/2019 | Gashgaee | |
| 12,292,129 | B2 * | 5/2025 | Haidt | F16K 7/126 |
| 2014/0061526 | A1 | 3/2014 | Watanabe et al. | |
| 2015/0369781 | A1 | 12/2015 | Zheng et al. | |
| 2021/0402082 | A1 | 12/2021 | Carlisle et al. | |

* cited by examiner

Fully closed

*Fully opened*

*marginally opened*

*Fully closed*

| | |
|---|---|
| 60 | Fluid Inlet |
| 61 | Fluid Outlet |
| 62<br>63 | Diaphragm |
| 63 | Control Pressure |
| 64 | Venturi |

Exposed surface area

Fully opened

Marginally opened

*Fig. 13*

| | Resultant Flow Behavior between port 16 and 18 | Schematic Figures | System (Net) Force balance |
|---|---|---|---|
| 131 | no flow | Figure 7 | 63 < 60 + 61 + 62 + 64 |
| 132 | no flow | Figure 7 | 63 < 60 + 61 + 62 + 64 |
| 133 | max flow | Figure 8 | 63 >> 60 + 61 + 62 + 64 |
| 134 | controlled flow from port 16 to port 18 | Figure 9 | 63 > 60 + 61 + 62 + 64 |
| 135 | controlled flow from port 18 to port 16 | Figure 9 | 63 > 60 + 61 + 62 + 64 |

| | |
|---|---|
| 60 | Fluid Inlet |
| 61 | Fluid Outlet |
| 62<br>63 | Diaphragm |
| 63 | Control Pressure |
| 64 | Venturi |

*Fig. 14*

| | Resultant Flow Behavior between port 16 and 18 | Schematic Figures | System (Net) Force balance |
|---|---|---|---|
| 141 | no flow | Figure 10 | 63 < 60 + 61 + 62 + 64 |
| 142 | max flow | Figure 11 | 63 >> 60 + 61 + 62 + 64 |
| 143 | controlled flow from port 16 to port 18 | Figure 12 | 63 > 60 + 61 + 62 + 64 |
| 144 | controlled flow from port 18 to port 16 | Figure 12 | 63 > 60 + 61 + 62 + 64 |

| | |
|---|---|
| 60 | Fluid Inlet |
| 61 | Fluid Outlet |
| 62<br>63 | Diaphragm |
| 63 | Control Pressure |
| 64 | Venturi |

PRESSURE CONTROLLED VALVE

FIELD OF THE INVENTION

Illustrative embodiments generally relate to medical devices and, more particularly, illustrative embodiments relate to controlling fluid flow with a medical valve.

BACKGROUND OF THE INVENTION

Fluid control medical valves are used in a wide variety of systems, such as intravenous infusion administration sets-whether in the hospital, clinic, or at home. Such valves are typically operated manually or with motorized actuators of some type that direct or restrict fluid flow.

SUMMARY OF VARIOUS EMBODIMENTS

In accordance with one embodiment, a medical valve has a housing forming a first port, a second port, and a control port, and a fluid channel within the housing between the first port and the second port. The valve also has

- a normally non-flat diaphragm at least partly within the housing and configured to isolate the control port from the fluid channel, first port, and the second port. The diaphragm is configured to control fluid flow through the fluid channel in response to four forces including:
  - i) a first force generated on the diaphragm from a differential fluid pressure between the first port and the control port times the exposed surface area of the diaphragm,
  - ii) a second force generated on the diaphragm from a differential fluid pressure between the second port and the control port times the exposed surface area of the diaphragm,
  - iii) a third force generated by elastic deformation of the diaphragm, and
  - iv) a fourth force generated by a pressure drop due to fluid flow in the fluid channel due to the Venturi effect.

To optimize production, the housing may be made from two separate pieces coupled together to form the fluid channel and at least partly encapsulate the diaphragm. In some embodiments, the diaphragm is configured so that an increase in inlet force increases fluid flow resistance through the fluid channel. In this case, the increased fluid flow resistance causes the fluid channel to be self-regulating to produce a regulated fluid flow rate. For example, the fluid channel may have an interior opening with an inner dimension, while the diaphragm has a stem extending through the interior opening. The stem has an outer dimension that is smaller than the interior opening inner dimension. Additionally, the stem is configured to selectively occlude fluid flow through the fluid channel.

Alternatively, the diaphragm may be configured so that an increase in inlet force decreases fluid flow resistance through the fluid channel. In a similar manner to other embodiments, the decreased fluid flow resistance causes the fluid channel to be self-regulating to produce a regulated fluid flow rate. To that end, in some embodiments, the housing may have a valve seat surrounding a given portion of the fluid channel. The diaphragm correspondingly has a sealing portion extending into the fluid channel that is normally seated against the valve seat and surrounds the given portion of the fluid channel. The fluid channel is closed when the sealing portion is seated against the valve seat. The flow resistance of the fluid channel between the first port and the second port also may change non-linearly with the displacement of the diaphragm.

The valve in a variety of embodiments thus may be configured to provide specific proportional fluid flow control in response to application of specific changes in the control force. To improve sealing bias, the diaphragm may have a normally convex portion with a convex surface in fluid communication with the control port. The normally convex portion forms a concave surface in fluid communication with the fluid channel and configured to have an increasing radius as the valve moves toward an open mode. The normally convex portion forms a pre-load bias toward the closed mode.

The fluid channel may be non-linear between the first port and the second port, and/or the first and second fluid ports may be substantially in-line.

In accordance with another embodiment, a method of controlling fluid flow through a valve couples tubing to a first port and to a second port of the housing of a valve in a closed mode, where housing forms a fluid channel between the first port and the second port. The method then manages, via a control port, a bias of a diaphragm with a shaped surface within the housing. The diaphragm is positioned in the housing to isolate the control port from the fluid channel, first port, and the second port. Next, the method applies a differential pressure between the first and second ports, and applies a control pressure to the control port to reduce the sealing force of the diaphragm. This application produces fluid flow through the fluid channel as the gland moves from a fully closed position to a partially opened position, and further to a fully open position.

To manage the diaphragm bias, the method may apply a positive pressure to the diaphragm via the control port. Alternatively, the method may apply a negative pressure to the diaphragm via the control port to manage the diaphragm. Also like some other embodiments, an increase in inlet force and increase or decrease fluid flow resistance, causing the flow channel to be self-regulating.

The diaphragm may have a normally convex portion with a convex surface in fluid communication with the control port as with other embodiments described here. The method may control the diaphragm to move toward an open mode, increasing the radius of the concave surface against the pre-load bias.

Preferably, fluid flow through the fluid channel is controlled in response to four forces including:

- i) a first force generated on the diaphragm from a differential fluid pressure between the first port and the control port times the exposed surface area of the diaphragm,
- ii) a second force generated on the diaphragm from a differential fluid pressure between the second port and the control port times the exposed surface area of the diaphragm,
- iii) a third force generated by elastic deformation of the diaphragm, and
- iv) fourth force generated by a pressure drop due to fluid flow in the fluid channel due to the Venturi effect.

Some embodiments of the method control pressures of between −8 to +15 PSIg to cause a corresponding change in fluid resistance in the fluid channel. As an example, some embodiments control pressure changes of less than or equal to 0.05 PSIg for opening periods of less than 50 mSec at differential inlet/outlet pressures of less than or equal to 1 PSId to yield a delivery of less than 5 mcL. Moreover, the shape of the elastically flexible diaphragm may provide a sufficient sealing force to block flow through the fluid channel with a pressure in the control port set to 0 PSIg.

In accordance with other embodiments of the invention, a medical valve has an open mode to permit fluid flow and a closed mode to prevent fluid flow. To that end, the medical valve has a housing forming a first port, a second port, a control port, and a fluid channel at least partly within the housing between the first port and the second port. The medical valve also has a diaphragm at least partly within the housing. The diaphragm has a normally convex portion with a pre-load bias toward the closed mode, and a convex surface in fluid communication with the control port. The normally convex portion preferably forms a concave surface in fluid communication with the fluid channel. To manage fluid flow, this concave surface is configured to have an increasing radius as the valve moves toward an open mode.

The diaphragm fluidly isolates the control port from the first port, the second port, and the fluid channel, and transitions from the closed mode to the open mode when subjected to a control pressure and a pressure difference between the first port and the second port. As such, the control port is configured to receive a prescribed pressure that changes the opening point of the valve.

The diaphragm may have a base seal region radially inward of at least a portion of the normally convex portion to receive a force from the normally convex portion to normally close the fluid channel. To improve sealing, the base seal region may have a base seal region average thickness that is greater than the convex region average thickness. The housing can have a valve seat surrounding a given portion of the fluid channel. Correspondingly, the diaphragm can have a sealing bead extending into the fluid channel and normally seated against the valve seat and surrounding the given portion of the fluid channel. As such, the fluid channel is closed when the sealing bead is seated against the valve seat.

The diaphragm may be configured to have a maximum rated open position, and the diaphragm may be biased to apply a closing-directed force even at the maximum rated open position. For example, the diaphragm may be biased to apply the closing-directed force at all positions as the diaphragm moves between the closed mode (i.e., when the valve is closed) and the maximum rated open position.

In some embodiments, the fluid channel is non-linear between the first port and the second port. Other embodiments may have a linear fluid channel. Moreover, the diaphragm may have a connection region secured between two portions of the housing; i.e., between a cap and a main portion. This valve therefore may be considered to form a three-piece valve in which the diaphragm fluidly isolates the control port from the fluid channel.

The diaphragm often may be considered to have three main areas: a proximal sealing region, a base region comprising the normally convex portion, and a connection region between the proximal sealing region and base region. As such, the diaphragm may be considered to form a unitary elastomeric component. Viewed in a similar or other manner, the diaphragm may have a base region movable proximally from a closed position toward a fully open position. Fluid flow through the fluid channel in the open mode varies between the closed position and the fully open position as a function of the position of the base region. Fluid flow through the fluid channel in the open mode also may increase as the base region of the diaphragm moves proximally from the closed mode toward the fully open position.

The control port may have a distally facing inner surface, while the diaphragm has a proximal portion adjacent to and spaced from the distally facing inner surface. In addition, or alternatively, the diaphragm may have a proximal opening region with an opening inner dimension for receiving a pressure, and a wall region adjacent to the proximal opening region and having a wall inner dimension. The wall inner dimension may be less than the opening inner dimension to form a seal when an instrument is inserted therein. To improve cost of production, the housing may be formed from two coupled sub-housings and the diaphragm may consist of a single unitary member. In this latter case, the valve may consist of a 3-piece assembly (i.e., no other independent parts to effectuate the valving function).

In accordance with another embodiments, a medical valve with open and closed modes has a housing forming a first port, a second port, a control port, and a fluid channel at least partly within the housing between the first port and the second port. The medical valve also has a diaphragm at least partly within the housing with a surface normally in fluid communication with the fluid channel. The diaphragm also has a base seal region radially inward of the concave surface and configured to receive a force to normally close the fluid channel. The normally concave surface is configured to have an increasing radius as the valve moves toward the open mode—the diaphragm preferably forms a pre-load bias toward the closed mode when in the open and closed modes.

The diaphragm fluidly isolates the control port from the first port, the second port, and the fluid channel, and transitions from the closed mode to the open mode when subjected to a prescribed control pressure and a pressure difference between the first port and the second port. Moreover, the control port is configured to receive a pressure controls the position of the normally concave surface to at least in part control fluid flow when in the open mode.

In accordance with other embodiments, a method controls infusion using a medical valve having an open mode to permit fluid flow and a closed mode to prevent fluid flow. To that end, the method secures the medical valve in the closed mode to an external liquid channel. The medical valve has a housing forming a first port, a second port, a fluid channel between the first and second ports, and a control port. The medical valve also has a diaphragm having a normally convex portion with a convex surface in fluid communication with the control port. The normally convex portion forms a concave surface in fluid communication with the fluid channel and forms a pre-load bias toward the closed mode. The diaphragm fluidly isolates the control port from the first port, the second port, and the fluid channel. The method also applies a given pressure to the control port to cause the radius of the concave surface to increase (i.e., the given pressure is sufficient to open the valve). The method further controls the given pressure to open the valve toward a maximum rated open position. To that end, the method may change flow resistance in the fluid channel between the first port and the second port as a function of the given pressure for the entire period between the closed mode toward the maximum rated open position.

In other embodiments, a medical diaphragm for a medical valve has a nozzle sealing region configured to receive a nozzle, a seal portion, and a connection region between the nozzle sealing region and the seal portion. The seal portion has a base seal region, a normally convex portion radially outward of the base seal region, and a securing portion radially outward of the normally convex portion. The diaphragm is formed from an elastomeric material as a unitary component. Moreover, the normally convex portion forms a normally concave portion with a radius that is configured to increase as the base seal region moves closer to the nozzle sealing region.

In accordance with other embodiments, a medical valve has a housing forming a first port, a second port, and a control port, and a fluid channel at least partly within the housing between the first port and the second port. A diaphragm at least partly within the housing has a normally convex portion with a convex surface in fluid communication with the control port. The normally convex portion forms a concave surface in fluid communication with the fluid channel. The concave surface is configured to have an increasing radius as the valve moves toward an open mode, while the normally convex portion forms a pre-load bias toward the closed mode.

The diaphragm fluidly isolates the control port from the first port, the second port, and the fluid channel. The diaphragm also is considered to have a minimum control pressure to transition from the closed mode to the open mode when subjected to a pressure difference between the first port and the second port. The diaphragm is configured so that a negative control pressure at the control port offsets the spring force from the elastic properties of the diaphragm. In a corresponding manner, the diaphragm is configured so that a positive control pressure at the control port offsets the spring force from the elastic properties of the diaphragm.

In accordance with other embodiments, a medical valve has a housing forming a first port, a second port, and a control port, and a fluid channel at least partly within the housing between the first port and the second port. The valve also has a diaphragm at least partly within the housing and configured to isolate the control port from the fluid channel, first port, and the second port. The valve is configured to control fluid flow through the fluid channel in response to five forces including:

a. an inlet force formed by inlet fluid pressure via the first port,
b. an outlet force formed by outlet fluid pressure via the second port,
c. the spring force (i.e., force applied by the diaphragm),
d. a control force formed by fluid pressure applied to the diaphragm via the control port, and
e. a venturi force formed by liquid flow through the fluid channel.

In some embodiments, the fluid diaphragm is configured so that an increase in inlet force increases fluid flow resistance through the fluid channel. This increased fluid flow resistance causes the fluid channel to be self-regulating (e.g., enables a controlled and consistent amount of fluid that passes through the valve per unit of time) to produce a regulated fluid flow rate (e.g., a controlled and consistent amount of fluid passing through the valve per unit of time). Alternatively, the fluid diaphragm may be configured so that a decrease in inlet force decreases fluid flow resistance through the fluid channel. In a manner like other embodiments, this decreased fluid flow resistance causes the fluid channel to be self-regulating to produce a regulated fluid flow rate. Preferably, in many cases, the valve is configured to provide specific proportional fluid flow control in response to application of specific changes in the control force.

Illustrative embodiments may combine various features noted above in any of a variety of permutations.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 13 is an exemplary table showing the fluid flow through the medical valve with a diaphragm in tension in response to various fluid and control pressures.

FIG. 14 is an exemplary table showing the fluid flow through the medical valve with a diaphragm in compression in response to various fluid and control pressures.

DESCRIPTION OF ILLUSTRATIVE EMBODIMENTS

In illustrative embodiments, a medical valve is configured for more precisely managed fluid flow into or out of a patient. To that end, the medical valve has a housing forming a fluid channel with two bi-directional fluid ports, and a control port that controls the fluid resistance through the fluid channel. A normally closed diaphragm within the housing provides the selective resistance to fluid flow. Specifically, application of a prescribed pressure (e.g., a positive or negative pressure) via the control port controls the diaphragm position in a precise manner to control the fluid flow rate through the fluid channel. Details of illustrative embodiments are discussed below.

Figure 1:
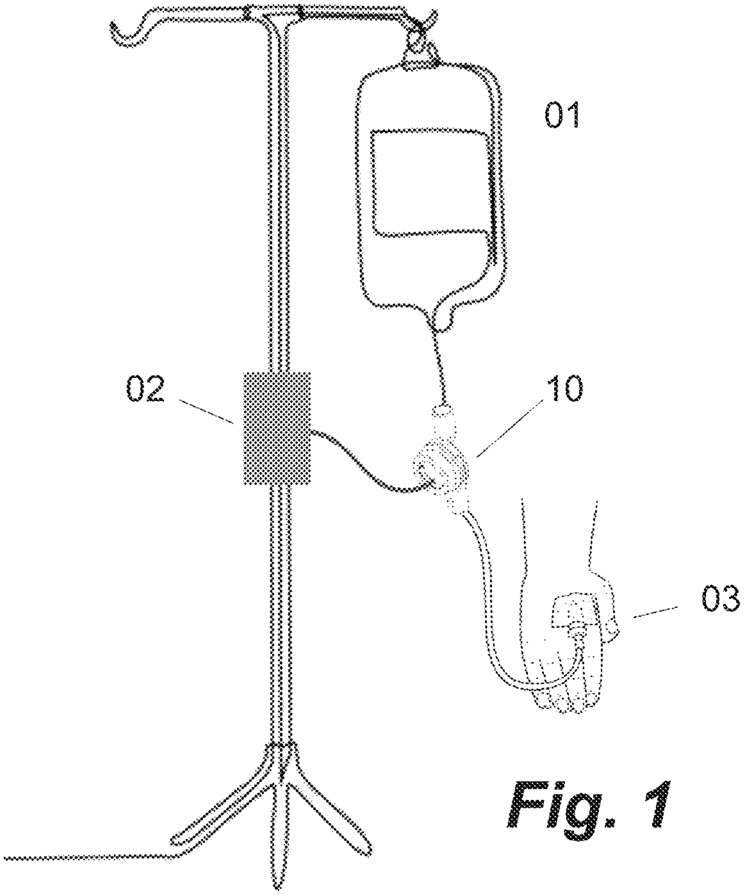
FIG. 1 schematically shows a medical valve in use in a system with a fluid source, a controller, and a patient in accordance with illustrative embodiments.

FIG. 1 schematically shows the normally closed medical valve 10 in a system in which source fluid 1 passes through a medical valve 10 and is controllably allowed to flow to a destination, such as a patient 3. The flow resistance of medical valve 10 is modulated by pressures coming from a pressure controller 2, which is configured to generate positive and/or negative pressure with precision (e.g., on the order of magnitude of about 0.001 PSI).

Figure 2A:
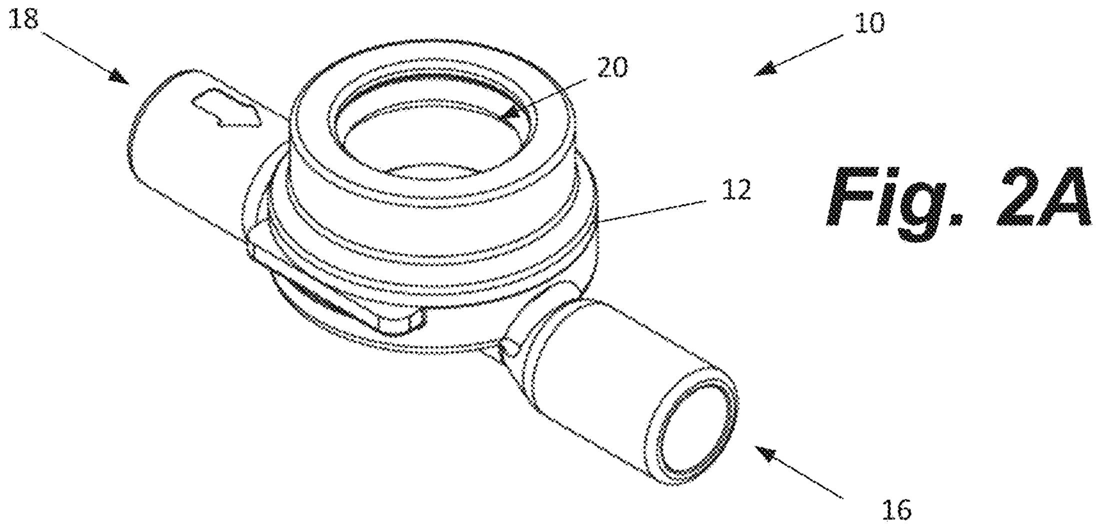
FIGS. 2A and 2B schematically show perspective views of a medical valve configured in accordance with illustrative embodiments.
Figure 2B:
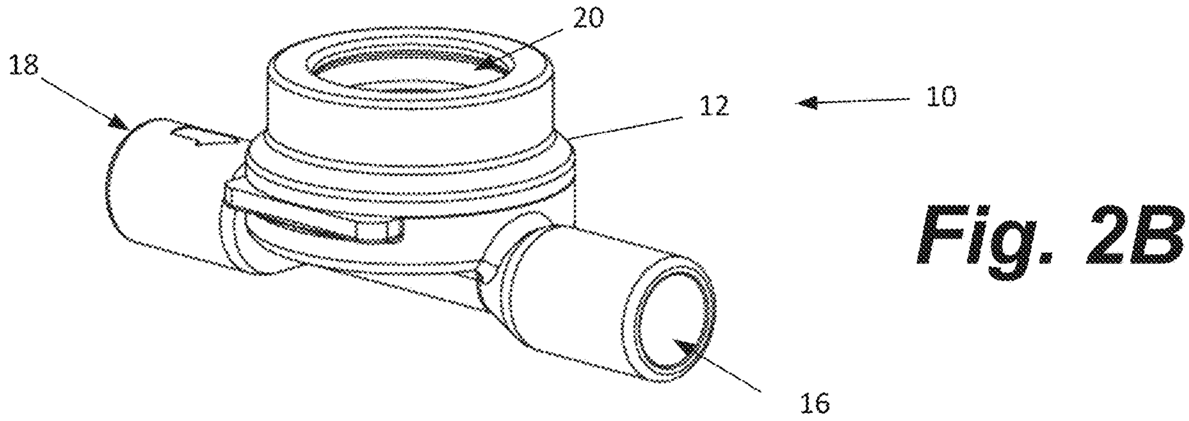

FIGS. 2A and 2B schematically show perspective views of the noted medical valve 10 configured in accordance with illustrative embodiments. The valve 10 has a housing 12 forming an internal fluid channel 14 (shown in FIG. 7 and others and discussed below) between a first port 16 and a second port 18. As shown, the two ports 16 and 18 can be in-line and/or permit flow in either direction. For example, at a first time, flow can be directed from the first port 16 to the second port 18, and at a subsequent time, flow can be directed from the second port 18 to the first port 16. Although the ports 16 and 18 may be in-line, various embodiments do not have an in-line or axially straight fluid channel 14.

Figure 3:
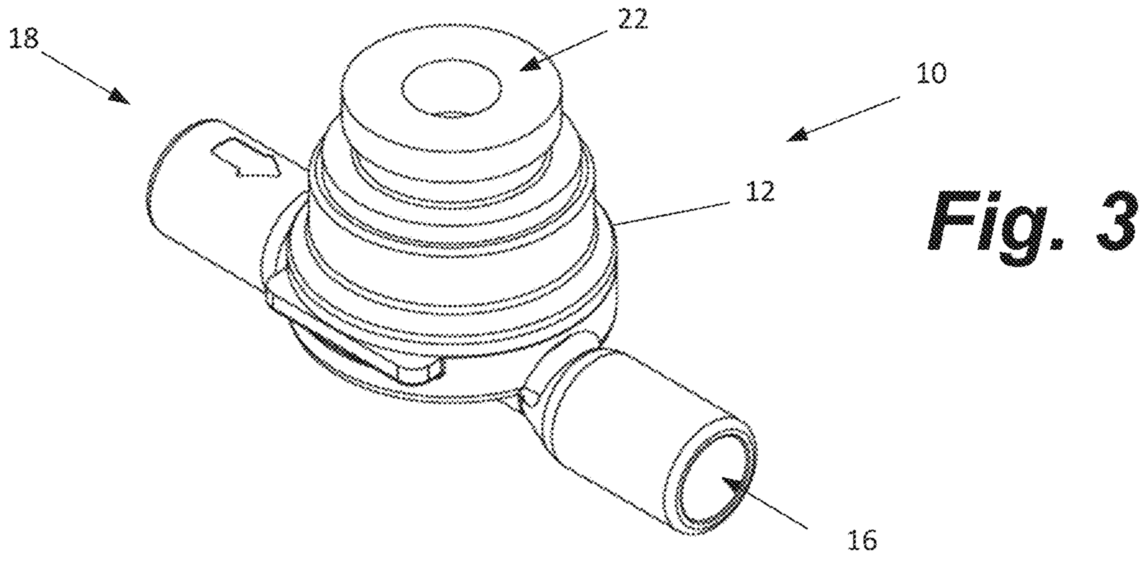
FIG. 3 schematically shows the valve of FIGS. 1 and 2 with an external nozzle in its control port in accordance with illustrative embodiments.

The housing 12 preferably is formed from biologically or chemically inert materials. For example, the housing 12 may be formed from a polymeric material, such as a hard plastic (e.g., polycarbonate), using conventional molding or printing processes. In illustrative embodiments, the housing 12 forms a third port, referred to as a "control port 20," which uses pneumatics to control fluid flow in a precise manner through the internal fluid channel 14, between the first and second ports 16 and 18. Specifically, the control port 20 may be used to communicate a control pressure from the controller 2 that changes the fluid flow resistance of the overall valve (discussed below). Among other things, that control pressure may be pneumatic or hydraulic. As shown, the control port 20 is open or otherwise configured to receive a nozzle 22 or other instrument (FIG. 3). This nozzle 22 communicates prescribed pressures (e.g., a positive or negative control pressure) that interact with movable components within the housing interior. This interaction controls fluid flow through the valve 10. Rather than using the nozzle 22, some embodiments may have a female connection that fits around the control port 20. Yet other embodiments may abuttingly and sealingly couple a nozzle to the top facing surface of the control port 20. In these latter embodiments, the two noted respective parts may apply a pressure to the control port 20.

The nozzle 22 may be a conventional or non-conventional nozzle used to provide some controlling pressure to the control port 20. For example, among other things, the nozzle 22 can be any one or more of a wall-pressure interface, a syringe, or a pressure interface of a controller pump. FIG. 3 schematically shows a nozzle 22 within the control port 20 as an example.

Figure 4:
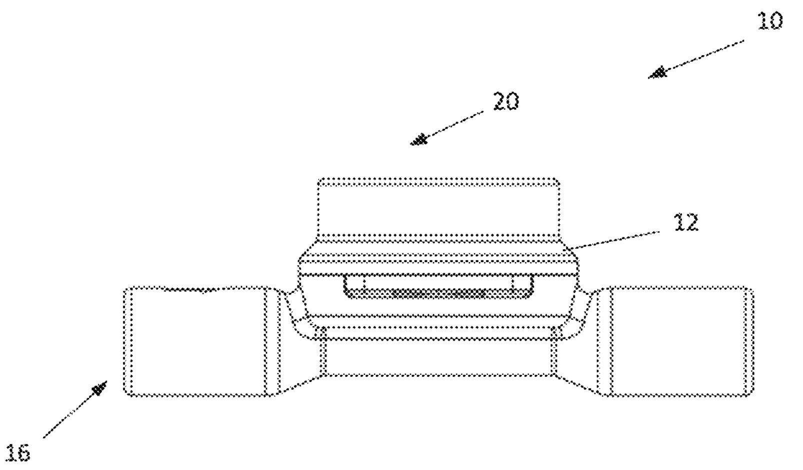
FIG. 4 schematically shows a side view of the medical valve of FIGS. 1 and 2 in accordance with illustrative embodiments.
Figure 5:
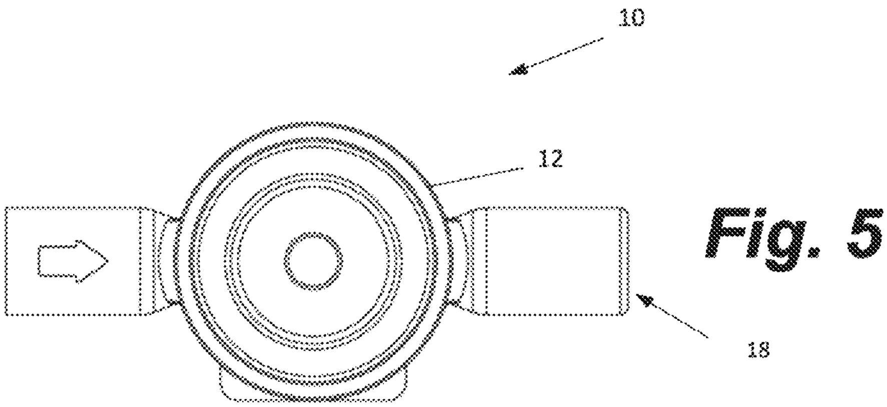
FIG. 5 schematically shows a top view of the medical valve of FIGS. 1 and 2 in accordance with illustrative embodiments.

FIG. 4 schematically shows a side view of the valve 10, while FIG. 5 schematically shows a plan view of the valve 10. Specifically, FIG. 5 shows straight down, into the control port 20 and some of its partially internal features. Those features are better shown in FIGS. 7-9, which show cross-sectional views of one embodiment of the valve 10 of FIG. 1 in different states (fully closed, fully opened, and marginally opened).

To control fluid flow, in response to input pressure via the control port 20, the valve 10 has an internal movable member 24 that moves in a largely controlled manner to vary fluid resistance between fluid ports 16 and 18. This member 24 generically may be considered to be a spring with a geometry, resilience, tensile strength, durometer, and/or elasticity customized to the application with which the valve 10 is intended to be used. In fact, the member 24 can have a symmetric or non-symmetric geometry as a function of the desired sealing and performance goals. As such, this spring may be referred to herein as a "diaphragm 24," which can be configured to a plurality of different applications, effectively producing different families/model types for the valve 10. For example, one family of valves 10 may be configured for lower flow rates (e.g., the pediatric population), while another family may be configured for higher flow rates (e.g., the adult population).

Figure 6:
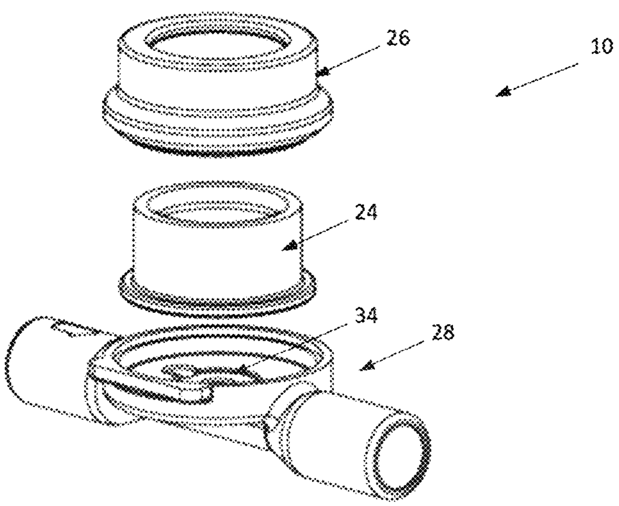
FIG. 6 schematically shows an exploded view of the valve of FIG. 1 in illustrative embodiments.

In illustrative embodiments, the diaphragm 24 is comprised of a biologically and/or chemically inert elastomeric member secured between two housing portions-a cap 26 and a main housing 28. As such, the valve 10 may at a basic level be a three-piece device, simplifying manufacture and design. FIG. 6 schematically shows an exploded view of these three elements 24, 26, and 28 to highlight this feature. Preferably, the entire valve 10 has no additional elements other than these three elements 24, 26, and 28. Indeed, some skilled in the art may add further components.

The simple, unitary diaphragm design may serve a number of functions. Among others, as suggested, the combination of its geometry and material properties may be tuned to provide a prescribed sealing force, cracking pressure, etc. Optionally, the diaphragm 24 can provide a sealing surface for a pneumatic control element. While illustrative embodiments may mold the diaphragm 24 in a single mold, other embodiments may mold the diaphragm 24 in different portions and assemble to create the noted unitary, monolithic diaphragm 24.

Figure 7:
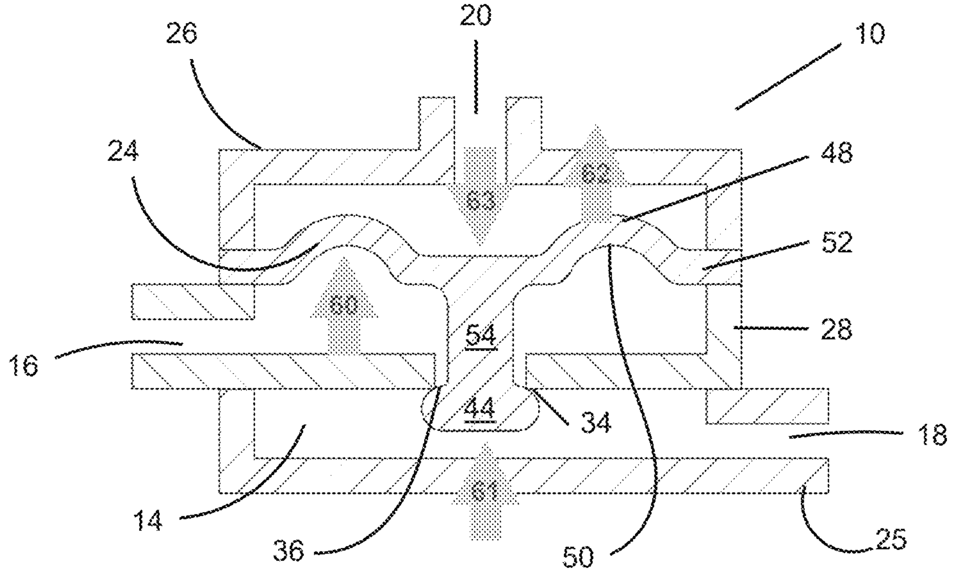
FIG. 7 schematically shows a simplified, cross-sectional view of an embodiment of the valve where a diaphragm has a stem and plug and is shown in a fully closed mode in accordance with illustrative embodiments of the invention.
Figure 8:
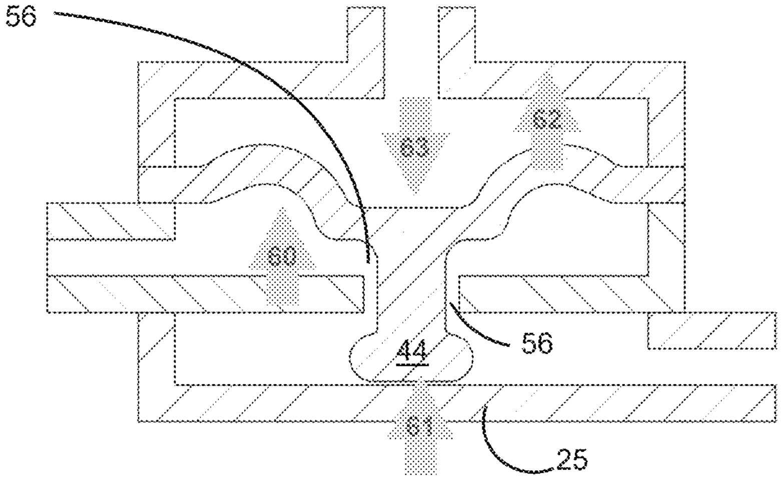
FIG. 8 schematically shows a simplified, cross-sectional view of the valve embodiment of FIG. 7 in a wide open/fully open mode in accordance with illustrative embodiments of the invention.
Figure 9:
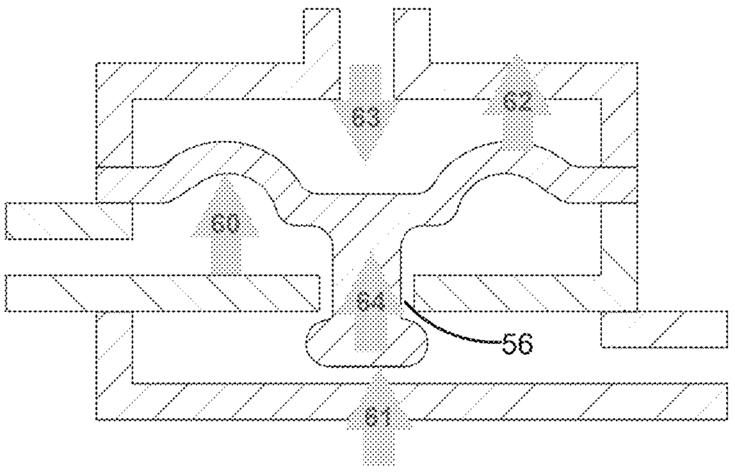
FIG. 9 schematically shows a simplified, cross-sectional view of the valve embodiment of FIG. 7 in a marginally/partially open mode in accordance with illustrative embodiments of the invention.
Figure 10A:
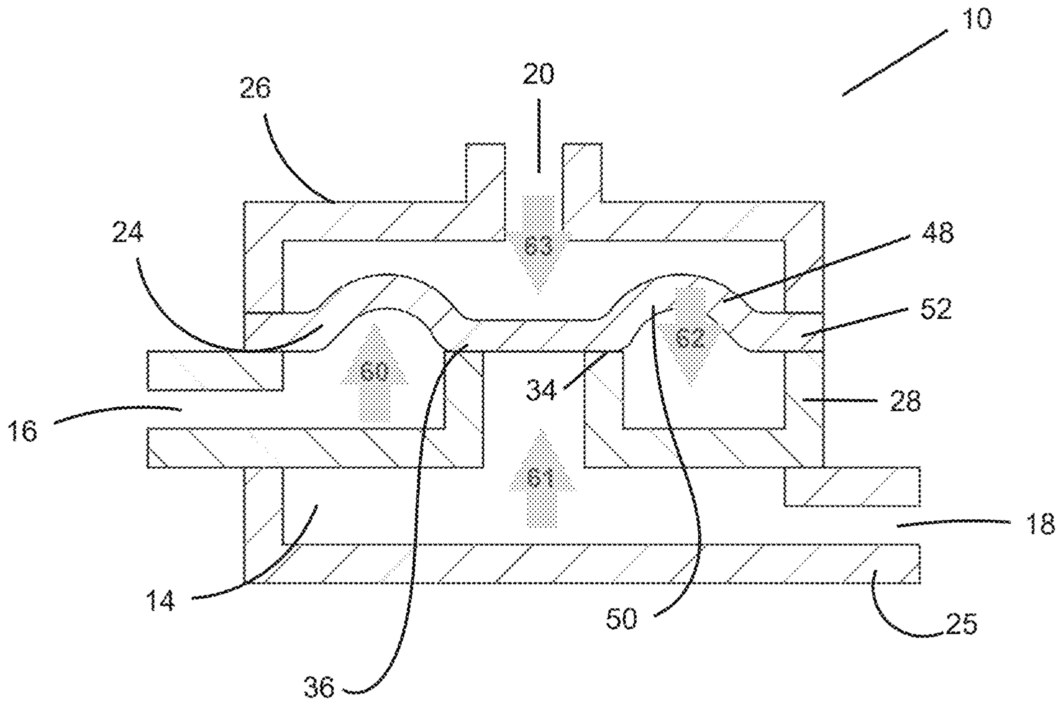
FIG. 10A schematically shows a simplified, cross-sectional view of an embodiment of the valve where the diaphragm has no stem or plug. This figure shows the valve in a fully closed mode in accordance with illustrative embodiments of the invention.
Figure 10B:
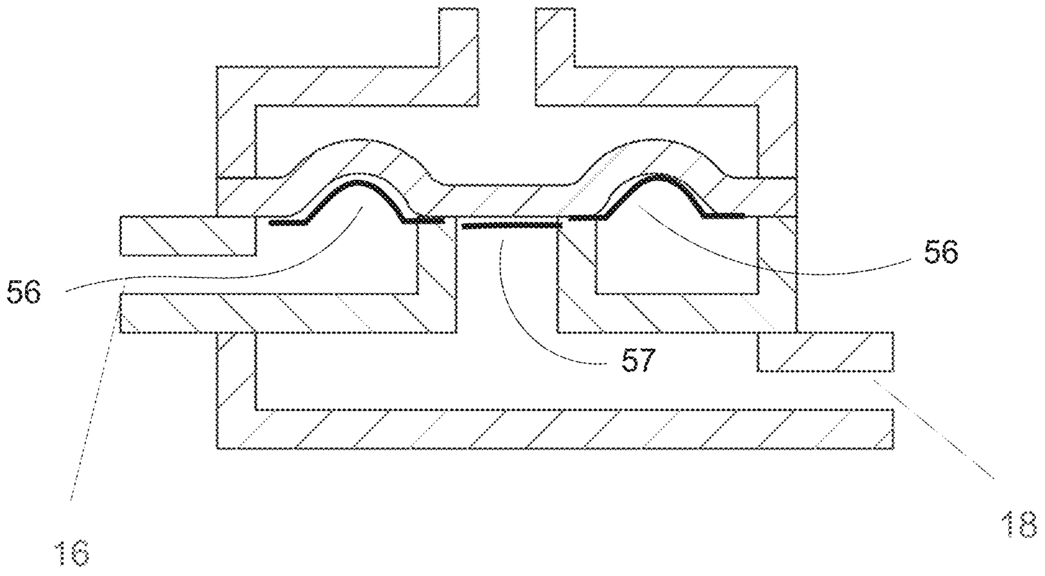
FIG. 10B schematically shows a simplified, cross-sectional view of an embodiment of the valve expressly showing the surface area exposed to pressure in the first port and the surface area exposed to the pressure in the second port.
Figure 11:
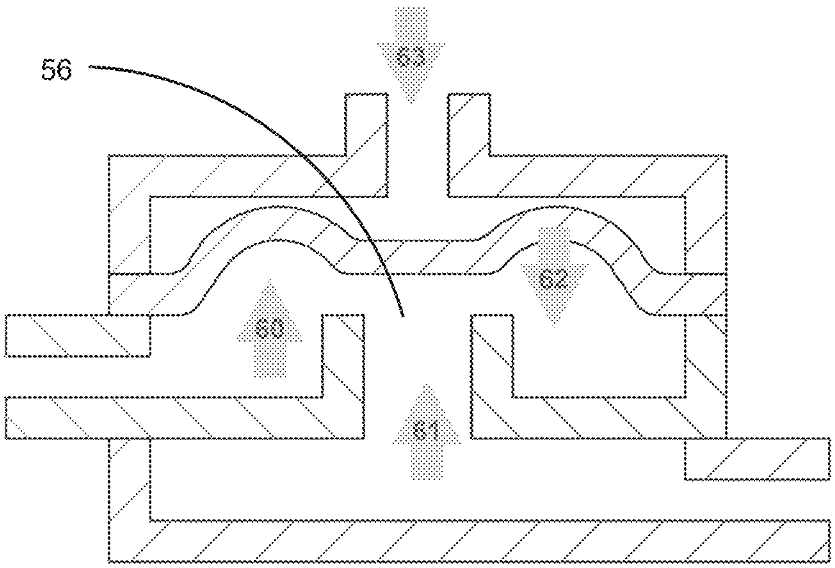
FIG. 11 schematically shows a simplified, cross-sectional view of the valve embodiment of FIG. 10A in a wide open/fully open mode in accordance with illustrative embodiments of the invention.
Figure 12:
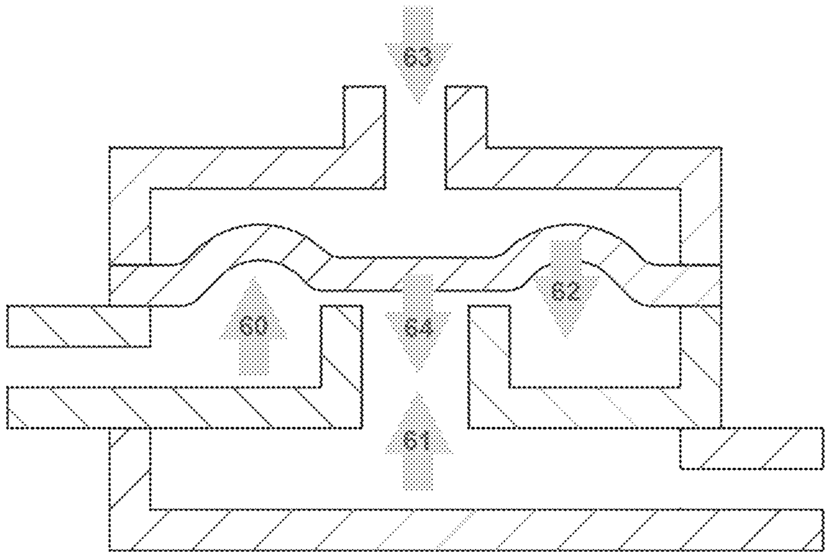
FIG. 12 schematically shows a simplified, cross-sectional view of the valve embodiment of FIG. 10A in a marginally/partly open mode in accordance with illustrative embodiments of the invention.

FIGS. 7-9 schematically show the diaphragm 24 with a stem and plug (one embodiment), while FIGS. 10-12 schematically show the diaphragm 24 without a stem or plug (another embodiment).

The diaphragm 24 may be considered to have details or a configured to a "formed" or "shaped" surface to have improved functional characteristics. These features or details may be pre-formed or molded into the diaphragm 24 or be a result of mechanical components urging it to have such details. For example, in illustrative embodiments, the diaphragm 24 has a normally convex portion 48 and a corresponding concave portion 50 preferably in a continuous, annular region circumscribing/surrounding a diaphragm base region 36 of the element 24. In other embodiments, however, those portions 48 and 50 are discontinuous, irregularly shaped, or another shape (e.g., elliptically shaped). They even may have discontinuities to control behavior of the diaphragm 24 under load. Accordingly, discussion of the annular, generally circular portions 48 and 50 are exemplary and not intended to limit various embodiments. Illustrative embodiments form the diaphragm 24 as a single unitary body.

To secure the diaphragm 24 within the interior of the valve 10, the diaphragm base region 36 of the diaphragm 24 has an integral securing portion 52 secured between the cap 26 and the main housing 28. This securing portion 52 cooperates with the convex region to fluidly isolate the control port 20 from the fluid channel 14 between the ports 16 and 18. As such, although the control port 20 receives pressures, it does not have fluid access to the fluid channel 14 between the ports 16 and 18, which in a medical context should be sterile. Accordingly, the diaphragm base region 36 divides the interior into two fluidly isolated portions: a fluid region through with fluid flows, and a control region that directly receives pressures via the control port 20. As noted below, the fluid region can include a part of the interior region formed by the diaphragm 24 and the main housing 28.

The cap 26 and main housing 28 may be coupled in any of a variety of conventional manners during a high-speed manufacturing process. For example, the cap 26 and main housing 28 may be ultrasonically welded. As another example, the cap 26 and main housing 28 may be connected via adhesive or UV curable material. As another example, the cap 26 and main housing 28 may be snap fit together.

The plug 44 extends through a sealing opening of the housing with an inner diameter. The outer dimension of the plug 44 is smaller than that inner diameter, enabling movement though the plug 44 through that sealing opening. The plug terminates in a bulbous portion that, when urged toward the control port 20, seals the valve 10. The gap between plug 44 and sealing surface 34 of main housing 28 produces a flow restriction through the valve. As such, when the diaphragm base region 36 of plug 44 sealingly abuts the sealing surface 34, there is no fluid flow.

In FIG. 10A, a top surface 26 of main housing 28 defines the maximum travel of diaphragm 24. The gap between the diaphragm base region 36 of diaphragm 24 and the sealing surface 34 of main housing 28 produces a flow restriction through the valve. As such, when the diaphragm base region 36 (sealingly) abuts the sealing surface 34, there is no fluid flow.

FIG. 10B schematically shows a simplified, cross-sectional view of an embodiment of the valve expressly showing the surface area exposed to pressure in the first port and the surface area exposed to the pressure in the second port. Specifically, in FIG. 10B, a pressure surface area (designated by reference number "56") of the diaphragm 24 is exposed to fluid pressure in port 16 and a pressure surface area 57 of diaphragm 24 is exposed to fluid pressure in port 18. In the configuration shown in FIG. 7, the first surface area 56 is shown as substantially larger than the second surface area 57. The movement of the diaphragm control element 24 is a function of the forces acting upon it, each force being the multiplicative factor of the pressure and the exposed surface area. So, in the instance when pressure in port 16 is the same magnitude yet opposite direction the pressure in port 18, the force 60 will be ratiometrically larger than the force 61 caused by pressure in port 18.

In FIGS. 7 and 10A, as the sealing surface 34 and diaphragm base region 36 increase in their distance from one another, the noted fluid flow is restricted proportionally less. At some point, the flow restriction becomes low enough that it is essentially a negligible factor in the overall resistance of the flow path. The fluid flow restriction can support a fully closed valve (FIG. 10A), a fully opened valve (FIG. 11), and intermediate/partially opened positions (FIG. 12). The gap between the sealing surface 34 and diaphragm base region 36 is a combination of five forces.

Referring to FIGS. 7-12: the pressure in port 16 generates Force 60; the pressure in port 18 generates Force 61; Force 62 is a feature of the diaphragm 24 that provides a force, or bias, to keep the two noted sealing surfaces 44 and 36 together, preventing fluid flow, and in illustrative embodiments, this Force 62 is generated from the use of the geometry of the formed elastomeric part; Force 63 is generated by the application of a separate control pressure applied to the valve 10, and in the circumstance where port 20 is open to atmosphere, force 63 will be, by definition, 0 PSIg and the sum of forces 60, 61, and 62 will be positive such that valve 10 will allow no flow; Force 64 is caused due to the Venturi Effect of the fluid flow itself as the fluid passes between the two sealing surfaces that creates a force that will urge the sealing surfaces together to close the flow path, based on the flow rate and viscosity of the fluid. Force 64 is only significant when a small part of the fluid channel 14, shown as "fluid channel 56," is small in FIGS. 9 and 12, and as soon as the valve is moderately opened, the Venturi Effect is diminished, and Force 64 becomes insignificant.

FIG. 13 is a table showing various states of relative absolute values of pressure with the resultant flow between fluid ports 16 and 18, based on force balances for the valve embodiment that has the diaphragm 24 with a stem and plug and is biased closed with the diaphragm in tension. In FIG. 13, (+) is interpreted as a positive gauge pressure, (–) is interpreted as a negative gauge pressure, (+/–) is interpreted as a positive or negative gauge pressure, and (0/–) is interpreted as a neutral or negative gauge pressure. Pressures in ports 16, 18, and 20 are ranked relative to the absolute value of pressure.

State 131 shows the effect when pressure in port 16, which generates a closing Force 60, is positive and greater than the also positive pressure in port 18, which generates a closing Force 61. The lesser neutral or absolute value of negative pressure in port 20 relative to both port 16 and port 18 produces a neutral or closing Force 63. The diaphragm 24 itself provides a constant structural closing Force 62, and the Venturi closing Force 64 is negligible when valve 10 is in a no flow state. This results in a system force balance where Force 63 is less than the net forces of 60, 61, 62, and 64 and a state of no flow through the valve 10 between port 16 and port 18. This state is shown in FIG. 7.

State 132 shows the effect when the absolute value of negative pressure in port 20, which generates a closing Force 63, is greater than the absolute value of negative pressure in port 16, which generates an opening Force 60. The lesser absolute value of negative pressure in port 18 relative to both port 20 and port 16 produces a neutral or opening Force 61. The diaphragm itself provides a constant structural closing Force 62, and the Venturi closing Force 64 is negligible when valve 10 is in a no flow state. This results in a system force balance where Force 63 is less than the net forces of 60, 61, 62, and 64 and a state of no flow through the valve 10 between port 16 and port 18. This state is shown in FIG. 7.

State 133 shows the effect when pressure in port 20, which generates an opening Force 63, is positive and greater than the positive pressure in port 16, which generates a closing Force 60. The lesser neutral or absolute value of negative pressure in port 18 relative to both port 20 and port 16 produces a neutral or opening Force 61. The diaphragm itself provides a constant structural closing Force 62, and the Venturi closing Force 64 is negligible when valve 10 is in a maximum flow state. This results in a system force balance where Force 63 is significantly greater than the net forces of 60, 61, 62, and 64 and a state of maximum flow through the valve 10 between port 16 and port 18. This state is shown in FIG. 8.

State 134 shows the effect when pressure in port 20, which generates an opening Force 63, is positive and greater than the positive pressure in port 16, which generates a closing Force 60. The lesser neutral or absolute value of negative pressure in port 18 relative to both port 20 and port 16 produces a neutral or opening Force 61. The diaphragm itself provides a constant structural closing Force 62, and the Venturi closing Force 64 is a slight closing force when valve 10 is in a controlled flow state. This results in a system force balance where Force 63 is greater than the net forces of 60, 61, 62, and 64 and a state of controlled flow through the valve 10 from port 16 to port 18. This state is shown in FIG. 9.

The fluid flow rate through valve 10 can be self-regulating even if pressure in Port 20 is held constant. Increasing pressure in Port 16 will increase closing Force 60 and increase fluid flow resistance, thereby keeping the flow rate change small relative to the pressure change. Decreasing pressure in Port 16 will decrease closing Force 60 and decrease fluid flow resistance, thereby keeping the flow rate change small relative to the pressure change. Accordingly, in illustrative self-regulating embodiments, the valve is configured to automatically adjust flow or pressure without requiring external control or manual intervention.

State 135 shows the effect when pressure in port 20, which generates an opening Force 63, is positive and greater than the positive pressure in port 18, which generates a closing Force 61. The lesser neutral or absolute value of negative pressure in port 16 relative to both port 20 or port 18 produces a neutral or opening Force 60. The diaphragm itself provides a constant structural closing Force 62, and the Venturi closing Force 64 is a slight closing force when valve 10 is in a controlled flow state. This results in a system force balance where Force 63 is greater than the net forces of 60, 61, 62, and 64 and a state of controlled flow through the valve 10 from port 18 to port 16. This state is shown in FIG. 9.

Referring to FIG. 14, various states of relative absolute values of pressure are shown with the resultant flow between fluid ports 16 and 18, based on force balances for the valve embodiment that has a diaphragm control element with no stem or plug. In FIG. 14, (+) is interpreted as a positive gauge pressure, (−) is interpreted as a negative gauge pressure, and (+/−) is interpreted as a positive or negative gauge pressure. Pressures in ports 16, 18, and 20 are ranked relative to the absolute value of pressure.

State 141 shows the effect when the pressure in port 20, which generates a closing Force 63, is positive and greater than the absolute value of positive or negative pressure in port 16, which generates an opening or closing Force 60. The lesser absolute value of positive or negative pressure in port 18 relative to both port 20 and port 16 produces an opening or closing Force 61. The diaphragm itself provides a constant structural closing Force 62, and the Venturi closing Force 64 is negligible when valve 10 is in a closed state. This results in a system force balance where Force 63 is greater than the net forces of 60, 61, 62, and 64 and a state of no flow through the valve 10 between port 16 and port 18. This state is shown in FIG. 10A.

State 142 shows the effect when pressure in port 16, which generates an opening Force 60, is positive and greater than the positive pressure in port 18, which generates an opening Force 61. The lesser absolute value of negative pressure in port 20 relative to the pressures of both port 16 and port 18 produces an opening Force 61. The diaphragm itself provides a constant structural closing Force 62, and the Venturi closing Force 64 is negligible when valve 10 is in a maximum flow state. This results in a system force balance where Force 63 is significantly less than the net forces of 60, 61, 62, and 64 and a state of maximum flow through the valve 10 between port 16 and port 18. This state is shown in FIG. 8.

State 143 shows the effect when pressure in port 16, which generates an opening Force 60, is positive and greater than the positive pressure in port 20, which generates a closing Force 63. The lesser positive pressure in port 18 relative to both port 20 and port 16 produces an opening Force 61. The diaphragm itself provides a constant structural closing Force 62, and the Venturi closing Force 64 is a slight closing force when valve 10 is in a controlled flow state. This results in a system force balance where Force 63 is less than the net forces of 60, 61, 62, and 64 and a state of controlled flow through the valve 10 from port 16 to port 18. This state is shown in FIG. 12.

Referring to State 143, the fluid flow rate through valve 10 can be somewhat self-regulating even if pressure in Port 20 is held constant. Increasing pressure in Port 16 will increase the fluid flow from 16 to 18, and thereby increase Force 64 from the Venturi Effect which will increase fluid flow resistance, thereby keeping the flow rate change small relative to the pressure change. Decreasing pressure in Port 16 will decrease the fluid flow from 16 to 18, and thereby decrease Force 64 from the Venturi Effect which will decrease fluid flow resistance, thereby keeping the flow rate change small relative to the pressure change.

State 144 shows the effect when pressure in port 18, which generates an opening Force 61, is positive and greater than the positive pressure in port 20, which generates a closing Force 63. The lesser positive pressure in port 16 relative to both port 20 and port 18 produces an opening Force 60. The diaphragm itself provides a constant structural closing Force 62, and the Venturi closing Force 64 is a slight closing force when valve 10 is in a controlled flow state. This results in a system force balance where Force 63 is less than the net forces of 60, 61, 62, and 64 and a state of controlled flow through the valve 10 from port 18 to port 16. This state is shown in FIG. 12.

It also should be noted that in various embodiments, the valve 10 is intended to be used once—it is a single-use device and therefore, disposable after a single use. The valve 10 therefore may be considered a biohazard after use. Moreover, as with other similar medical device, the valve 10 should be sterilized (e.g., gamma or EtO) after it is manufactured and wrapped in a sterile package.

Figure 15:
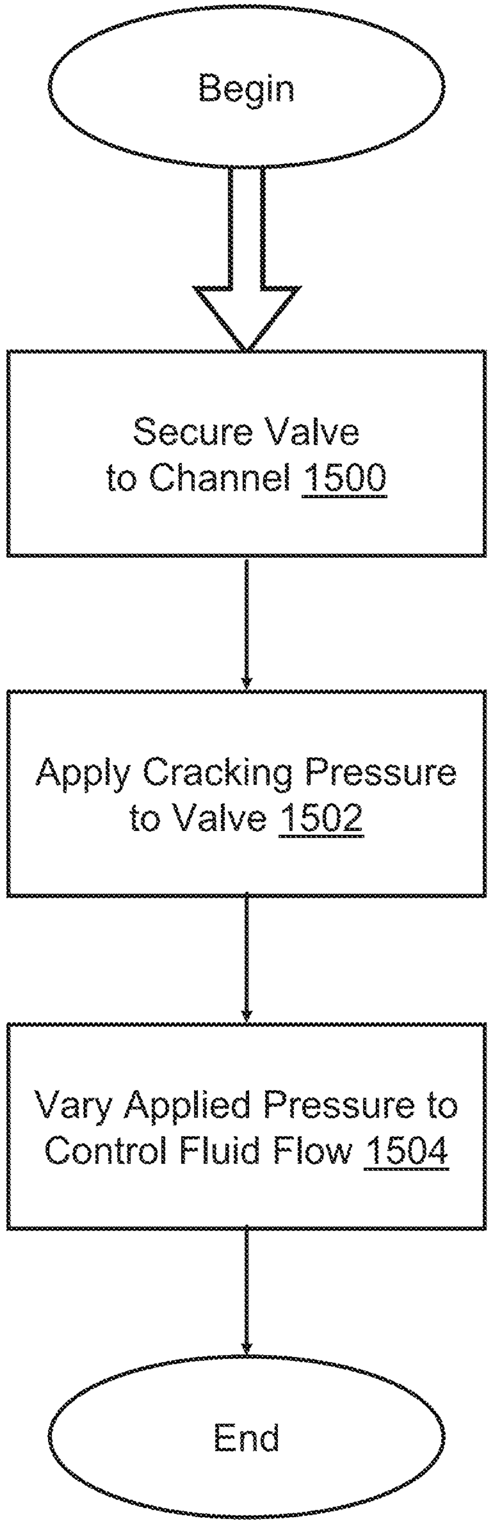
FIG. 15 shows a valve control process in accordance with illustrative embodiments.

The process of FIG. 15 begins at step 1500, in which a clinician, patient, caregiver, or other end user secures the valve 10 to the fluid channel between ports 16 and 18. For example, the user may secure tubing coupled with a fluid bag on a hospital pole to the first port 16. In a corresponding manner, the user may secure tubing from the second port 18 into a Luer lock or similar securing mechanism. This Luer lock may be coupled to extension tubing secured to the patient's vasculature (e.g., via a cannula). Of course, those skilled in the art may couple the valve 10 in any of a variety of different manners, whether to a patient or device and as such, discussion of this specific connection is exemplary and not intended to limit various embodiments. In addition, the user also couples a pressure source from the controller 2 to the control port 20. At this initial phase, the pressure source may be off.

After all the connections are made and other pre-use preparation is completed, the valve 10 is ready to use and fluid may flow from the bag toward the valve 10. The process is explained in step 1502, in which a "cracking" pressure is applied to the valve 10/diaphragm 24. More specifically, as known by those in the art, the cracking pressure of a valve 10 is the minimum control pressure required to initially open a given valve 10—the fluid differential pressure at which flow ensues, described in States 135, 142, 143, and 144.

Next, at step 1504, the process varies the applied pressure to the control port 20 to control fluid flow between ports 16 and 18. This variation may simply increase pressure to assist with further opening the valve 10. In illustrative embodiments, the diaphragm 24 is configured so that it responds in a predictable manner when subjected to pressure changes (through the control port 20) of on the order of 0.01 PSI. In other words, fluid flow may be finely controlled in small increments (e.g., on the order of about 0.1 mL per hour), corresponding to pressure changes of 0.01 PSI input in the control port 20. Other embodiments may not be so fine. For example, the valve 10 may be tuned to incrementally respond to pressures of 0.05 PSI, 0.10, 0.15, etc.

Figure 16:
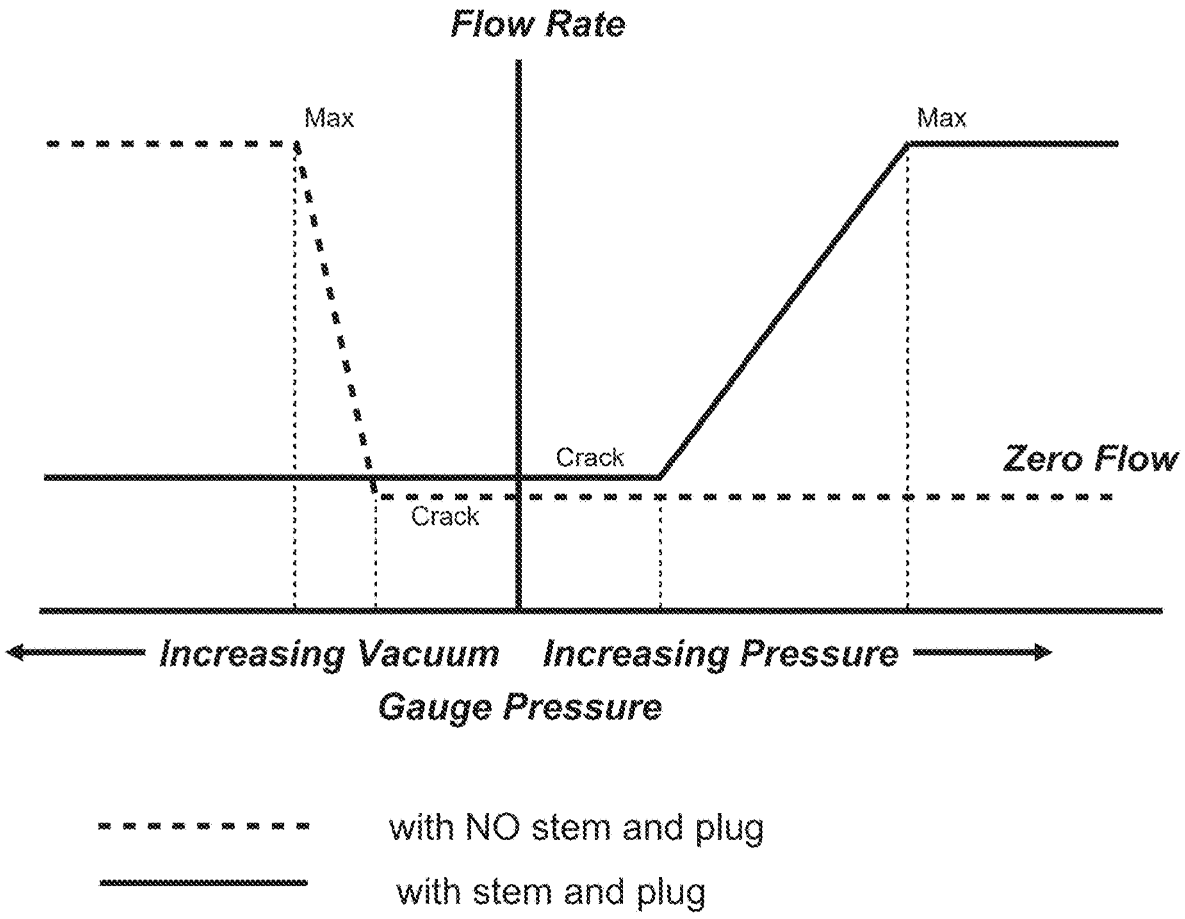
FIG. 16 graphically shows an opening sequence of either of the noted valves in accordance with illustrative embodiments.

FIG. 16 graphically shows an example of the operation of the valve 10 in FIG. 1. In this figure, the X-axis represents the amount of positive gauge pressure applied to the control port 20, while the Y-axis represents the flow between ports 16 and 18 in the valve 10. As shown for the diaphragm 24 with stem and plug denoted by a solid line, the valve 10 may remain closed until the control pressure in port 20 attains a positive pressure such that a cracking pressure is achieved to permit flow. At that point, the fluid flow will increase (due to reducing fluid resistance in the valve 10) to a maximum flow rate. After achieving the maximum flow rate, the flow will remain substantially constant even with increasing control pressure 20. The behavior follows a similar path for the reverse direction along the same solid line with increasing vacuum control pressure 20 as the valve 10 transitions from the open mode (i.e., when the diaphragm 24 is positioned to permit maximum fluid flow between ports 16 and 18) to zero flow between ports 16 and 18.

As shown for the diaphragm 24 with no stem or plug denoted by a dotted line, the valve 10 may remain closed until the control pressure in port 20 attains an increasing vacuum pressure such that a cracking pressure is achieved to permit flow. At that point, the fluid flow increases (due to reducing fluid resistance in the valve 10) to a maximum flow rate. After achieving the maximum flow rate, the flow will remain substantially constant even with increasing the vacuum of control pressure 20. The behavior follows a similar path for the reverse direction along the same dotted line with increasing control pressure 20 as the valve 10 transitions from the open mode (i.e., when the diaphragm 24 is positioned to permit maximum fluid flow between ports 16 and 18) to zero flow between ports 16 and 18. Note that the control pressure 20 may be set by controller 2 to a value well below and above atmospheric pressure (e.g., in the range of −8 to +15 PSIg).

In FIG. 16, the solid line for the diaphragm 24 with a stem and plug exhibits a different slope between Zero Flow and Max Flow than the dotted line for the diaphragm 24 with no stem or plug.

Note that the slope of the line in FIG. 16 can be configured to rise at a more gradual rate, or at a gentler rate, as a function of selected specifications of the diaphragm 24. As noted, the durometer, geometry, elasticity, etc. may be selected and tested to ensure the desired flow rates and sensitivities. In some embodiments, rather than being constant, the slope can be non-constant and change at various points. Other embodiments may have a non-linear or combination linear slope between the opening point and the maximum flow point.

In additional embodiments, the diaphragm 24 geometry can be asymmetrical to provide differences in proportional flow control. In a similar manner, flow performance can be asymmetric based on a number of things, such as the direction of flow. As an example, the diameter of stem 54 may be tapered to provide a non-linear gap between the sealing surface 34 and diaphragm base region 36.

Figure 17A:
FIG. 17A-17D schematically show various embodiments of diaphragm designs with concave portions relative to the fluid channel.
Figure 17B:
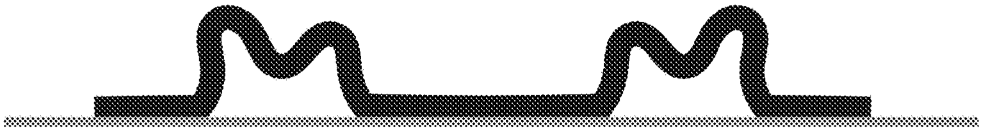
Figure 17C:
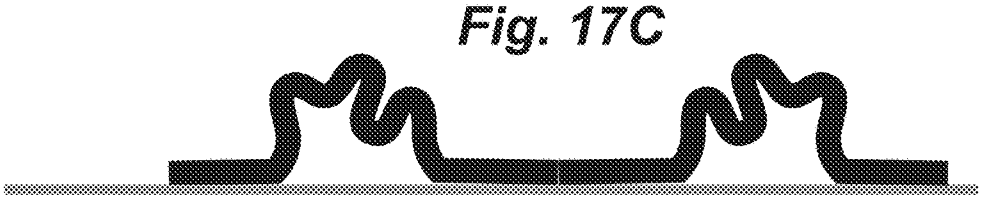
Figure 17D:

FIG. 17A-17D schematically show various embodiments of diaphragm designs with concave portions relative to the fluid channel 14. FIG. 17A, for example, shows macro-concave portions, while FIGS. 17B and 17C also show macro-concave portions with irregular/non-symmetrical shaping—e.g., interior concavities and convex portions in this figure. Specifically, the embodiments of FIGS. 17B and 17C are concave overall despite having details that are not necessarily concave. Preferably, the diaphragm material is pre-formed with the concavities. FIG. 17D shows another embodiment in which the concavity may be created by applying a force to a normally generally flat diaphragm 24 by a mechanical member (e.g., by a valve seat). In some such embodiments, the generally flat diaphragm is normally urged against the mechanical member to produce the concavity.

It should be noted that while infusion therapy has been discussed, those skilled in the art can use the various valve embodiments in a number of other medical applications, such as dialysis or drug compounding. Accordingly, discussion of infusion therapy is not intended to limit various other embodiments. In a similar manner, some embodiments may apply in a non-medical context, such as laboratory fluid control.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A medical valve comprising:

a housing forming a first port, a second port, and a control port configured to receive an externally applied positive and/or negative control pressure;

a fluid channel within the housing between the first port and the second port; and a normally non-flat diaphragm at least partly within the housing and configured to isolate the control port from the fluid channel, first port, and the second port, the diaphragm having an exposed surface area, the diaphragm configured to control fluid flow through the fluid channel in response to four forces including:

i) a first force generated on the diaphragm from a differential fluid pressure between the first port and the control port times the exposed surface area of the diaphragm, ii) a second force generated on the diaphragm from a differential fluid pressure between the second port and the control port times the exposed surface area of the diaphragm, iii) a third force generated by elastic deformation of the diaphragm, and iv) a fourth force generated by a pressure drop due to fluid flow in the fluid channel due to the Venturi effect.

2. The medical valve as defined by claim 1 wherein the housing comprises two separate pieces coupled together to form the fluid channel and at least partly encapsulate the diaphragm.

3. The medical valve as defined by claim 1 wherein the diaphragm is configured so that an increase in inlet force increases fluid flow resistance through the fluid channel, the increased fluid flow resistance causing the fluid channel to be self-regulating to produce a regulated fluid flow rate.

4. The medical valve as defined by claim 3 wherein the fluid channel includes an interior opening with an inner dimension, further wherein the diaphragm has a stem extending through the interior opening, the stem having an outer dimension, the stem outer dimension being smaller than the interior opening inner dimension, the stem configured to selectively occlude fluid flow through the fluid channel.

5. The medical valve as defined by claim 1 wherein the diaphragm is biased closed with the diaphragm in compression.

6. The medical valve as defined by claim 5 wherein the housing has a valve seat surrounding a given portion of the fluid channel, further wherein the diaphragm has a sealing portion extending into the fluid channel and normally seated against the valve seat and surrounding the given portion of the fluid channel, the fluid channel being closed when the sealing portion is seated against the valve seat.

7. The medical valve as defined by claim 1 wherein the diaphragm forms a fluid-tight barrier separating (i) a control chamber in fluid communication with the control port from (ii) the fluid channel, such that there is no fluidic communication between the control chamber and the fluid channel.

8. The medical valve as defined by claim 1 wherein the valve has an open mode and a closed mode, the diaphragm having a normally convex portion with a convex surface in fluid communication with the control port, the normally convex portion forming a concave surface in fluid communication with the fluid channel, the concave surface configured to have an increasing radius as the valve moves toward the open mode, the normally convex portion forming a pre-load bias toward the closed mode.

9. The medical valve as defined by claim 1 wherein the flow resistance of the fluid channel between the first port and the second port changes non-linearly with the displacement of the diaphragm.

10. The medical valve as defined by claim 1 wherein the first and second fluid ports are substantially in-line.

11. A medical valve comprising:

a housing forming first means for porting fluid, second means for porting fluid, and controlling means for receiving a positive or negative pressure;

channeling means for channeling fluid within the housing between the first porting means and the second porting means; and sealing means configured to isolate the pressure means from the channeling means, the first porting means and the second porting means, the sealing means having a sealing means force, the sealing means configured to control fluid flow through the channeling means in response to four forces including:

i) a first force generated on the sealing means from a differential fluid pressure between the first porting means and the controlling means times the exposed surface area of the sealing means, ii) a second force generated on the sealing means from a differential fluid pressure between the second porting means and the controlling means times the exposed surface area of the sealing means, iii) a third force generated by elastic deformation of the sealing means, and iv) a fourth force generated by a pressure drop due to fluid flow in the fluid channel due to the Venturi effect.

12. The medical valve as defined by claim 11 wherein the sealing means is configured so that an increase in inlet force increases fluid flow resistance through the channeling means, the increased fluid flow resistance causing the channeling means to be self-regulating to produce a regulated fluid flow rate.

13. The medical valve as defined by claim 12 wherein the channeling means includes stem receiving means with an inner dimension, further wherein the sealing means has a stem extending through the stem receiving means, the stem having an outer dimension, the stem outer dimension being smaller than the stem receiving means inner dimension, the stem configured to selectively occlude fluid flow through the channeling means.

14. The medical valve as defined by claim 11 wherein the sealing means is biased closed with the sealing means in tension.

15. The medical valve as defined by claim 11 wherein the housing has a valve seat surrounding a given portion of the channeling means, further wherein the sealing means has a sealing portion extending into the channeling means and normally seated against the valve seat and surrounding the given portion of the channeling means, the channeling means being closed when the sealing portion is seated against the valve seat.

16. A method of controlling fluid flow through a valve, the method comprising:

coupling tubing to a first port and to a second port of a housing of a closed valve, the housing forming a fluid channel between the first port and the second port;

managing, via a control port configured to an externally applied positive and/or negative control pressure, a bias of a diaphragm having a shaped surface, the diaphragm positioned in the housing to isolate the control port from the fluid channel, first port, and the second port;

applying a differential pressure between the first and second ports; and applying a control pressure to the control port to change the sealing force of the diaphragm, applying comprising producing fluid flow through the fluid channel as the diaphragm moves from a fully closed position to a partially opened position, and further to a fully open position.

17. The method as defined by claim 16 wherein managing the diaphragm bias comprises applying a positive pressure to the diaphragm via the control port.

18. The method as defined by claim 16 wherein managing the diaphragm bias comprises applying a negative pressure to the diaphragm via the control port.

19. The method as defined by claim 16 further comprising increasing inlet force via the first port to increase fluid flow resistance through the flow channel, the increased fluid flow resistance causing the fluid channel to be self-regulating to produce a regulated fluid flow rate.

20. The method as defined by claim 16 wherein the diaphragm is biased closed with the diaphragm in tension.

21. The method as defined by claim 16 wherein the valve has an open mode and a closed mode, the diaphragm having a normally convex portion with a convex surface in fluid communication with the control port, the normally convex portion forming a concave surface in fluid communication with the fluid channel, the concave surface configured to have an increasing radius as the valve moves toward an open mode, the normally convex portion forming a pre-load bias toward the closed mode, the method further controlling the diaphragm to move toward an open mode, controlling comprising increasing the radius of the concave surface against the pre-load bias.

22. The method as defined by claim 16 wherein fluid flow through the fluid channel is controlled in response to four forces including:

i) a first force generated on the diaphragm from a differential fluid pressure between the first port and the control port times the exposed surface area of the diaphragm, ii) a second force generated on the diaphragm from a differential fluid pressure between the second port and the control port times the exposed surface area of the diaphragm, iii) a third force generated by elastic deformation of the diaphragm, and iv) fourth force generated by a reduced static pressure at a throat of a Venturi section of the fluid channel, the Venturi sect on comprising a converging region, the throat, and a diverging region, the reduced static pressure being generated during fluid flow through the throat.

* * * * *